Figure 1:
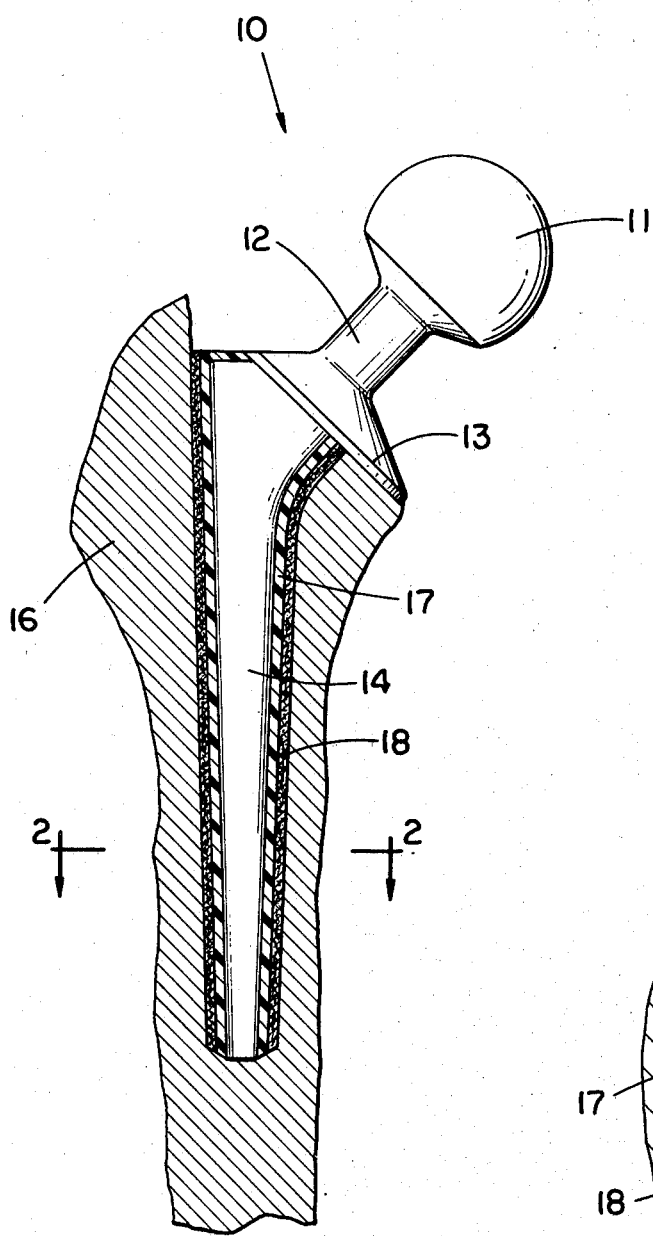

United States Patent [19]

McDaniel et al.

[11] 4,454,612
[45] Jun. 19, 1984

[54] PROSTHESIS FORMATION HAVING SOLID AND POROUS POLYMERIC COMPONENTS

[75] Inventors: John M. McDaniel; Niles L. Noblitt, both of Warsaw, Ind.

[73] Assignee: Biomet, Inc., Warsaw, Ind.

[21] Appl. No.: 291,427

[22] Filed: Aug. 10, 1981

Related U.S. Application Data

[63] Continuation-in-part of Ser. No. 147,374, May 7, 1980.

[51] Int. Cl.³ .............................................. A61F 1/24
[52] U.S. Cl. ...................................... 3/1.913; 3/1.91; 128/92 C; 128/92 CA; 427/2
[58] Field of Search .................................. 3/1.9–1.913; 128/92 C, 92 CA; 433/173–175, 201

[56] References Cited

U.S. PATENT DOCUMENTS

| | | | |
|---|---|---|---|
| 3,938,198 | 2/1976 | Kahn et al. | 3/1.913 X |
| 3,986,212 | 10/1976 | Sauer | 3/1.91 |
| 3,987,499 | 10/1976 | Scharbach et al. | 3/1.91 |
| 4,118,532 | 10/1978 | Homsy | 3/1 X |
| 4,129,470 | 12/1978 | Homsy | 3/1.91 X |
| 4,164,794 | 8/1979 | Spector et al. | 3/1.91 X |
| 4,213,816 | 7/1980 | Morris | 3/1.91 X |

FOREIGN PATENT DOCUMENTS

| | | | |
|---|---|---|---|
| 2306552 | 8/1974 | Fed. Rep. of Germany | 3/1.91 |
| 2444831 | 9/1975 | Fed. Rep. of Germany | 3/1.91 |

*Primary Examiner*—Ronald L. Frinks
*Attorney, Agent, or Firm*—Barnes & Thornburg

[57] ABSTRACT

A prosthesis having a porous polymeric coating over a non-porous polymeric substrate is disclosed. The porous polymeric coating is constructed by forming a mass of randomly arranged fibers of polymeric material in contact with a non-porous polymeric substrate of a compatible material. The entire prosthesis and mass of fibers is enclosed in a mold with interior dimensions conforming to the intended shape of the article. The mold is then subjected to an elevated temperature for sufficient time to sinter the fibers of the mass to each other and to the underlying substrate yet leave a pore volume of about 50%. The preformed material is ultra-high molecular weight polyethylene. Preferred sintering conditions are also disclosed.

6 Claims, 2 Drawing Figures

PROSTHESIS FORMATION HAVING SOLID AND POROUS POLYMERIC COMPONENTS

This is a continuation-in-part of application Ser. No. 147,374, filed May 7, 1980.

This invention relates generally to prosthetic devices employed as high-strength artificial bone implants designed to promote a strong union with the bone matter into which such devices are implanted. More specifically, this invention relates to prosthetic devices which include a layer or coating of porous polymeric material intended for bone tissue ingrowth to enhance the bone-prosthesis union.

Prosthetic devices of the prior art having porous surface components to provide for bone tissue infusion are well known. The porous surface components have been made of various materials including metals, ceramics, and polymers. These surface components have, in turn, been secured by various means to a multitude of structural cores formed of various metals.

Prosthetic devices in which a titanium metal core or pin is provided with a porous coating formed of metallurgically bonded, titanium metal fibers are disclosed in Rostoker et al U.S. Pat. No. 3,906,550. A pioneer disclosure of the use of porous metal coatings on a metal core is made in Hahn U.S. Pat. No. 3,605,123. Tronzo U.S. Pat. No. 3,808,606 and Tronzo U.S. Pat. No. 3,843,975 further disclose various porous metal coatings on a metal core, the coatings having varying porosity with various pore sizes.

Prosthetic devices having porous ceramic surfaces are disclosed in Smith U.S. Pat. No. 3,314,420; Scharbach U.S. Pat. No. 3,987,499; and German Offenlegungsschrift 2,306,552. The porous ceramic surfaces therein disclosed can consist of more than one layer of ceramic material applied to a metal core, and the layers can have differing porosities.

Prosthetic devices having porous polymeric coatings have been developed more recently to overcome the shortcomings of both metal and ceramic coatings. In the Dow Corning German Offenlegungsschrift 24 44831, there was disclosed a prosthesis coated with a biologically neutral elastomer, preferably silicone rubber. Kahn U.S. Pat. No. 3,938,198 further disclosed reinforcing a silicone rubber with a fabric of polyethylene terephthalate (Dacron) to strengthen the elastomer, the fabric preferably being a velour, the fibers of which protruded through the outer surface of the elastomeric coating to enhance tissue ingrowth.

Sauer U.S. Pat. No. 3,986,212 discloses a polymeric coating of porous high density polyethylene and polypropylene and mixtures thereof. The coating is said to be applied by surrounding a core with powdered polymer and heating until cured to form a coating with an internal network of interconnected pores. The tortuosity of the pores - a measure of length to diameter of the paths through the pores - is said to be important in evaluating the probable success of such a coating in use on a prosthetic device. Morris U.S. Pat. No. 4,213,816 further disclosed the application of a porous polytheylene coating to a non-porous polyethylene substrate coating on a metal core to increase the bonding strength between the metal core and the porous coating. The porous coating was applied in the form of a powder and the article as a whole subjected to an elevated temperature which would bond the powder to the substrate. Certain criteria are disclosed for selecting the correct polymer for the substrate and powder coating based on the melt index of each.

An excellent analysis of the prior art is to be found in Spector U.S. Pat. No. 4,164,794 in which he concludes that porous coatings of polymers such as polyethylene, even high-density polyethylene, do not establish the proper biomechanical environment to achieve appropriate early fixation, long-term stability, and strength at the bone-prosthesis interface. The prior art materials are said to lack the toughness, creep resistance, tensile and impact strength, and steam sterilizability necessary of prosthetic device coatings. Spector discloses a porous coating of polysulfone formed by a sintering technique, whereby particles of polysulfone are heated for a period of time and at a temperature sufficient to cause particle fusion at one or more contact points to provide a porous continous composite coating on an inner load-bearing functional prosthetic device component. Other polymers such as high-density polyethylenes are said to be incapable of being fabricated into a satisfactory material using Spector's process due to the lack of satisfactory mechanical properties.

Spector points out that the bone ingrowth in porous orthopedic implants can be considered as a two-stage phenomenon. Each stage is influenced by the pore characteristics and biomechanical characteristics of the implant. In the first stage and immediately after implantation, the porous component fills with a blood clot which subsequently becomes "organized." Fibroblasts appear in the clot region and fibrogenesis occurs. The clot is replaced by loose connective tissue and capillaries. At this point, preosteoblasts begin to appear in the peripheral pores of implant. These cells can become osteoblasts or chondroblasts, depending upon the environment. If the original pore size of the implant is too small or if the pore structure has been distorted by the initial applied loads, one or more of the above sequence of events can be interrupted. For example, it is generally believed that a smaller pore size ($<90\mu$) leads to the ultimate formation of fibrous tissue, not bone, in the implant. If the modulus of the material is too low, micromotion occurs with loading. This would lead to an environment that is conductive to fibrous or cartilage tissue, not bone, formation. For example, excessive motion can lead to disruption of vascularity and a decrease in oxygen, a condition which favors cartilage formation.

After bone has filled the pores of the implant, in the second stage it undergoes remodeling which is influenced primarily by its biomechanical environment. Spicules in the implant which experience uniform stress will thicken, while those spicules which experience no stress or excessive stress (stress concentration) are resorbed. The modulus of metals and ceramics is so high that the implants do not deform under the applied loads. The bone spicules in these porous implants thus do not experience sufficient load to thicken. Bone trabeculae in these higher modulus porous materials tend to resorb, becomming thinner than the spicules in the porous implants which are the subject of this invention.

The above discussion indicates that the biomechanical environment established by the implant material and the geometry of the porous substrate have a profound effect on the biological fate of implants. It has now been found that a delicate balance must be achieved between parameters affecting load transmission, micro-motion, dimensional stability, and strength. The transmission of stress to the bone in the pores of a coated prosthetic device should optimally mimic the physiological biomechanical environment of the normal bone repair process.

It is, therefore, an object of the present invention to provide efficacious prosthetic devices composed of an inner load bearing functional components, a non-porous encapsulating coating and a porous polymeric outer coating which will provide the optimum biomechanical environment to achieve a long-term bone fixation by ingrowth of tissue into and through the porous coating. Another object of the present invention is to provide a process for preparing a two-layered coating on prosthetic devices which will provide an ideal biomechanical environment for the ingrowth of tissue and its subsequent transformation to bone.

The objects of the present invention are achieved by sintering a lamination of fibrous polymeric material to an underlying non-porous coating encapsulating the structual element of a prosthetic device. While a sintered, fibrous polyeric material is disclosed for use in a filter in Rudolph U.S. Pat. No. 2,297,248, none of the voluminous literature on porous layer prosthetic devices discloses a high density polymeric material as an encapsulating coating for a metal component, with a fibrous polymeric porous coating laminated, by sintering, to the encapsulating material to form the outer surface of a prosthesis.

The preferred polymeric material for both the high-density, encapsulating layer and for the sintered, porous, outer layer is high-density or ultra-high molecular weight polyethylene (UHMWPE), an example of a suitable medical grade, commercially available material being Hercules #1900, supplied by Hercules Inc., Wilmington, Del. Polymeric porous coatings, such as UHMWPE, have advantages over porous metal coatings when applied to metal load-bearing members or stems forming a prosthesis. Bone invasion of the porous structure is dependent upon a close fit between the porous coated stem and the prepared cavity in the bone which accommodates the prosthesis. Any free space or gaps in the fit result in undesirable fibrous tissue invasion of the porous coating, rather than bone invasion. With a rigid metal porous coating, the fit must, therefore, be extremely precise. With the somewhat resilient UHMWPE coating of the present invention, the cavity can be prepared slightly undersize to ensure close conformity between the cavity and the prosthesis inserted therein.

Corrosion products inherently given off by metals and the metal ion sensitivity of a patient are difficulties avoided by the use of a resilient polymeric coating. UHMWPE, in vivo, gives off no corrosion products. Should it be necessary, removal of a porous metal-coated prosthesis can be quite difficult. With a porous polymeric-coated prosthesis, however, the coating can be cut or the entire stem forceably extracted.

Some of the advantages of polymeric materials over metals, such as its stability in vivo, are well recognized. However, heretofore, the use of a porous polymeric coating on metal prosthetic devices had encountered difficulty in achieving a satisfactory bond between the coating and the metal device. Even where the metal structural element is enclosed or surrounded by the porous coating, the attachment is primarily adhesive or by mechanical interlock. The relatively low strength of the porous coating prevents effective fixation to the metal of the structural portion of the prosthesis.

In practicing the present invention, the metal stem or load-bearing member of the prosthesis is mechanically encapsulated by the solid, non-porous polymeric, preferably UHMWPE, layer. The encapsulating attachment is effective because the mechanical strength of the solid UHMWPE is relatively high. After this attachment by encapsulation has been completed, the compressed, fibrous polymer (forming the outer porous layer) is sintered both inter-fiberally and to the solid polymer layer. In this second attachment, the bond between the solid polymer and the fibers of the porous polymer are of the same order of strength as the bond between the sintered fibers within the porous polymer.

Figure 2:
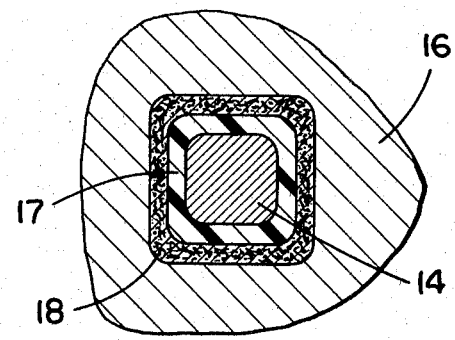

The present invention can be used in connection with a broad range of prosthetic devices of which the total hip prosthesis shown in the accompanying drawing is merely illustrative. Other prosthetic devices, not shown, are within the scope of the teachings of this invention, as will be apparent from the following description and examples of the preferred embodiment of the invention. In the accompanying drawings:

FIG. 1 is a side sectional view of a typical hip prosthesis embodying the present invention; and FIG. 2 is a sectional view taken along the line 2—2 of FIG. 1.

As shown in FIGS. 1 and 2, a hip prosthesis 10 includes a ball head 11 (sized to fit into a matching acetabular socket) carried on a neck 12. The neck 12 extends from a platform 13 carried by a primary load-bearing member in the form of a stem 14. The stem 14 may be formed of titanium, or other suitable metal, and may have various cross-sectional configurations, here shown as square (FIG. 2). The structure so far described will be recognized as conventional.

The structure differs from the conventional and achieves the objects of the present invention in that the stem, or that portion of it adjacent bone tissue 16, is provided with a non-porous, encapsulating coating, or over-layer 17, which is formed of a high-density polymer, preferably UHMWPE, applied by compression molding around the stem component. This solid coating preferably has a thickness of approximately one and one-half millimeters. Because the coating 17 tightly encloses the cross section of stem 14, the attachment between the stem and the coating is mechanically strong.

Overlying the encapsulating coating 17 is a somewhat resilient mat of polymer fibers 18 which provide a field for bone growth intrusion. The contiguous fiber areas are bonded to each other and to the coating 17. The fiber mat 18 tightly fills the space in the prepared bone cavity between the coating 17 and the adjacent cavity wall. The depth or thickness of the fiber layer preferably is approximately one and one-half millimeters, and the layer is of generally uniform density across its thickness.

As previously mentioned, the high-density polymer preferred for forming the prosthesis is commercially available high-density polyethylene or medical grade UHMWPE. The fibers can be formed by shredding solid bars of the polymer and the touching points or areas of the fiber bonded to each other and to the encapsulating coating simultaneously in a sintering operation. Satisfactory temperature parameters for the sintering cycle have been found to be in the range of 250° F. to 400° F. for a time period dependent upon the size and form of the device. The sintered fiber outer material 18 can be shaped to tightly engage the adjacent bone cavity walls to minimize the formation of collagenous tissue at the bone-prosthesis interface and to maximize bone growth intrusion into the open pores of the fiber mat. Fiber lengths should be between one centimeter and two-tenths centimeters to permit convenient handling of the fibers and provide, when sintered, a satisfactory mat of fibrous consistency. A satisfactory cross-section diameter for the fibers has been found to be in the range of one-tenth to five-tenths millimeters. A porosity range for the sintered mat can be 25% to 75%, with, 50% porosity a preferred value.

To achieve the desired biomechanical properties for the porous component, it may be desirable to control the fiber aspect ratio (the ratio of length to mean diameter of the fibers) and the sintering conditions based on the material selected. The fiber size and aspect ratio is believed to determine in part the pore size and therefore the elasticity and tensile strength. The optimum aspect ratio appears to be about 20 for fibers of commercially available medical grade UHMWPE.

As indicated, the sintering conditions are also important to achieve the desired properties. Satisfactory sintering of the fibers to the underlying non-porous layer of polymer can be accomplished by placing a mass of fibers around the article to be coated and inserting the article into a metal mold having an interior configuration matching the dimensions of the intended article. The mold is then heated to a temperature greater than the glass transistion temperature, $T_g$, of the polymer employed. This sintering temperature is held constant, or nearly so, for a time sufficient for permanent bonds to form at junctures of the fibers, and between the fibers and the underlying non-porous polymeric substrate.

Essentially no pressure is applied during the sintering process other than the pressure of initial compaction of the fibers to conform with the interior configuration of the mold and that induced by the differential thermal expansion of the materials within the mold. The pressure of initial compaction disappears during the sintering process due largely to the creep of the polymer of the fibers at the elevated temperature.

EXAMPLE I

To prepare a fibrous mat for use in the sintering process, a round bar of Hercules #1900 UHMWPE of about 2 inches in diameter is shredded by subjecting the bar to the shaving action in a lathe of a square-faced cutter, the bar rotating at a speed of approximately 500 r.p.m The fibers thus formed are observed to be continuous in length and a cross-section diameter of from 0.1 mm to 0.5 mm. The long fibers are then cut to a length of about ½ cm.

The shredded fiber is randomly arranged into a loose mass. The loose mass is then subjected to compression to approximately 25% of full density for about 30 minutes. On inspection, the mat now appears as a medium-density felt with a thickness of about 0.3 cm. On microscopic examination, the fibers of the mat appear to assume a tortous path defining therebetween a porous network of spaces.

A section of the mat is then cut and placed to conform as a single layer around a prosthesis as shown in FIGS. 1 and 2 which has previously had a non-porous UHMWPE coating bonded thereto. The dimensions of the wrapped section of the prothesis corresponds roughly to the desired finished dimensions. The fiber-covered prosthesis is placed in a mold of either stainless steel or aluminum having interior dimension closely matching the prosthesis. The mold is then heated for about 65 minutes at a temperature of between 280°–340° F.

The sintered fibrous polymeric coating thus produced is observed to achieve the objects of the present invention. The typical pore size of the coating was approximately 500 microns, while the pore volume is approximately 50%.

The fibrous mat, as described above, has substantial compliance, that is, deformation under compressive stress and, although the surface area presented to the body's environment is much greater than would be the case with a solid implant, there are no corrosion product problems with UHMWPE as might occur with a fibrous metal outer layer with the same extended surface area. If required, the prosthesis may be fixed in place for the short term, that is, for the time interval required to accomplish strengthening bone intrusion, by utilizing a conventional methyl-methacrylate bone cement applied, preferably, to an area of the bone-prosthesis interface which has no polymeric coating interposed.

While the invention has been shown in detail in the drawings and described in the foregoing description and example, the same is considered to be illustrative and not restrictive in character, it being understood that only the presently preferred embodiment has been shown and described and that all changes and modifications that come within the spirit of the invention as claimed are desired to be protected.

We claim:

1. A prosthesis adapted for fixation in mammalian bone structure by natural growth intrusion of bone into the surface of the prosthesis over a time interval, said prosthesis comprising a load-bearing member, a non-porous encapsulating coating of high density polyethylene enclosing at least a portion of said member, and a mass of randomly arranged high density polyethylene fibers overlying said encapsulating coating to provide a field for said bone growth intrusion having a porosity of about 50%, the contiguous points of the fibers being bonded to each other and to said encapsulating coating.

2. A prosthesis as claimed in claim 1 in which said high density polyethylene is ultra-high molecular weight polyethylene.

3. A prosthesis as claimed in claim 1 in which both said encapsulating layer and said mass have a thickness of the order of one and one-half millimeters.

4. A mammalian skeleton prosthesis comprising a metal load-bearing member, an encapsuluating coating of ultra-high molecular weight polyethylene on said member, and an over-layer on said encapsulating coating having a porosity of about 50%, said over-layer being formed by a mass of ultra-high molecular weight polyethylene fibers, the contiguous strands of said fiber mass being bonded by sintering to each other and to said encapsulating coating.

5. A prosthesis as claimed in claim 4 in which both said encapsulating coating and said over-layer have a thickness of the order of one and one-half millimeters.

6. A hip prosthesis comprising a ball head adapted for insertion into an acetabular socket, a neck connected to said ball head and a load-bearing metal stem projecting from said neck adapted for reception in the intramedulary cavity of a femur, an encapsulating coating of ultra-high molecular weight polyethylene on said stem, and a resilient over-layer on said encapsulated stem, said over-layer having a porosity of about 50% and being formed by a mat of ultra high molecular weight polyethylene fibers, the contiguous points on the strands of said fiber mat being bonded by sintering to each other and to said encapsulating coating.

* * * * *